United States Patent
Rustum et al.

(10) Patent No.: US 10,073,072 B2
(45) Date of Patent: Sep. 11, 2018

(54) DISSOLUTION OF HYDROPHOBIC API, INCLUDING AVERMECTINS WITH OR WITHOUT OTHER API SUCH AS PYRANTEL, FROM A COMPLICATED MATRIX DOSAGE FORM

(71) Applicant: MERIAL, INC., Duluth, GA (US)

(72) Inventors: Abu M. Rustum, Flemington, NJ (US); Satish Kumar, Piscataway, NJ (US); Andrew L. McAdoo, Howell, NJ (US)

(73) Assignee: MERIAL INC., Duluth, GA (US)

( * ) Notice: Subject to any disclaimer, the term of this patent is extended or adjusted under 35 U.S.C. 154(b) by 97 days.

(21) Appl. No.: 14/872,639

(22) Filed: Oct. 1, 2015

(65) Prior Publication Data

US 2016/0097753 A1    Apr. 7, 2016

Related U.S. Application Data

(60) Provisional application No. 62/058,450, filed on Oct. 1, 2014.

(51) Int. Cl.
| | |
|---|---|
| *G01N 33/15* | (2006.01) |
| *C09K 3/00* | (2006.01) |
| *G01N 30/06* | (2006.01) |
| *G01N 13/00* | (2006.01) |

(52) U.S. Cl.
CPC .............. *G01N 33/15* (2013.01); *C09K 3/00* (2013.01); *G01N 30/06* (2013.01); *G01N 2013/006* (2013.01)

(58) Field of Classification Search
CPC .................. G01N 33/15; G01N 2013/006
See application file for complete search history.

(56) References Cited

U.S. PATENT DOCUMENTS

| | | | | |
|---|---|---|---|---|
| 5,100,889 | A * | 3/1992 | Misra | C07C 17/16 514/365 |
| 2002/0004244 | A1* | 1/2002 | Avdeef | G01N 21/33 436/171 |
| 2003/0236203 | A1 | 12/2003 | Freehauf | |
| 2004/0110844 | A1* | 6/2004 | Takahata | A61K 31/165 514/625 |
| 2004/0115837 | A1 | 6/2004 | Schapaugh et al. | |
| 2014/0094465 | A1* | 4/2014 | Sun | A61K 31/08 514/239.5 |

OTHER PUBLICATIONS

K. Gowthamarajan: "Dissolution Testing for Poorly Soluble Drugs: A Continuing Perspective", Dissolution Technologies, vol. 17, No. 3. Jan. 1, 2010.

S Vandhana et al. "Evaluation of suitable solvents for testing the anti-proliferative activity of triclosan—a hydrophobic drug in cell culture", Indian journal of biochemistry & biophysics, Jun. 1, 2010 {Jun. 1, 2010), pp. 166-171.

* cited by examiner

*Primary Examiner* — Paul Sang Hwa Hyun
(74) *Attorney, Agent, or Firm* — Judy Jarecki-Black; John Ezcurra; Merial Inc.

(57) ABSTRACT

This disclosure describes the results of the studies conducted to develop a dissolution method to monitor release profiles of hydrophobic active pharmaceutical ingredients such as ivermectin with or without pyrantel pamoate from a drug product made of complex matrix that includes, but is not limited to beef, tallow, corn cob and soy protein.

14 Claims, 1 Drawing Sheet

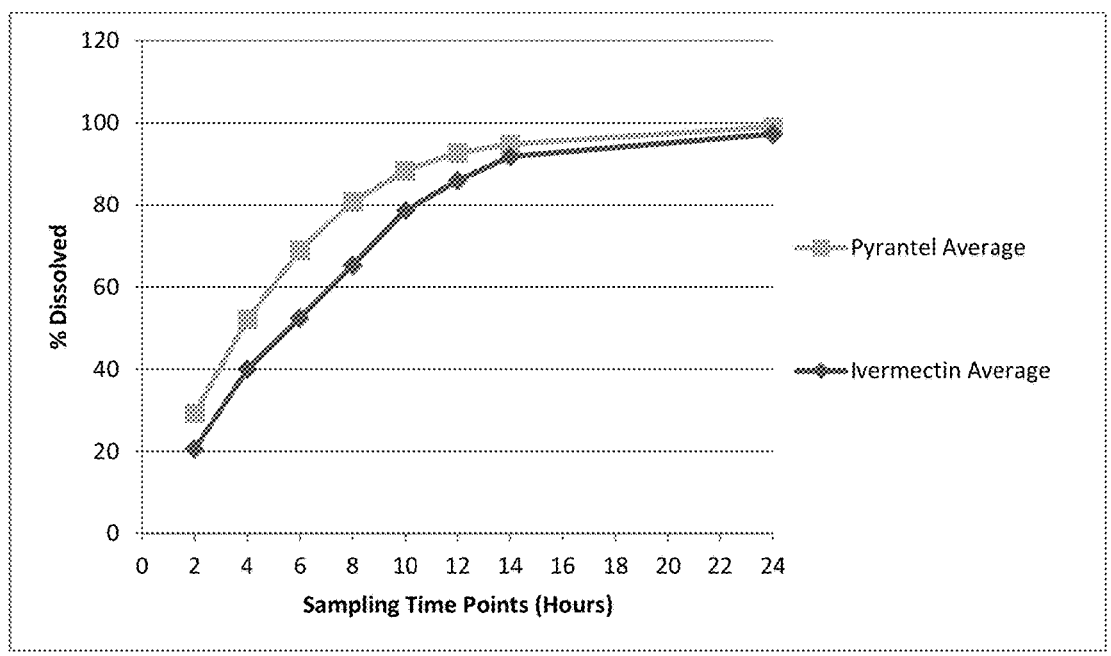

DISSOLUTION OF HYDROPHOBIC API, INCLUDING AVERMECTINS WITH OR WITHOUT OTHER API SUCH AS PYRANTEL, FROM A COMPLICATED MATRIX DOSAGE FORM

CROSS-REFERENCE TO RELATED APPLICATIONS

This application claims benefit of U.S. Provisional Application No. 62/058,450, filed on 1 Oct. 2014, and incorporated herein by reference in its entirety.

FIELD OF THE INVENTION

The invention generally relates to the field of dissolution measurement and, more particular to methods and compositions for reproducible dissolution testing of complicated, matrix-style pharmaceutical dosage forms.

BACKGROUND OF THE INVENTION

A solid pharmaceutical composition or dosage form, such as a tablet or capsule, is generally composed of a mixture of active ingredient(s) and excipient(s). The reproducibility of the adsorption of an active ingredient (drug) from a solid composition form after oral administration depends on several factors such as the release of the drug from the composition and the dissolution or solubilization of the drug under physiological conditions. Because of the critical nature of the release of the drug from the composition and the dissolution or solubilization of the drug, a dissolution test is highly relevant to the prediction of the in vivo performance of a drug. Drug approving authorities such as the FDA and EMA often require pharmaceutical companies to determine the drug release characteristics of any new pharmaceutical composition in order to obtain approval. These tests can also be required as an USP quality parameter, to assess batch-to-batch quality of a pharmaceutical composition, for accepting products, waiving bioequivalence requirements or supporting requests for other bioequivalence requirements than the recommended.

Various protocols have been developed for conducting the in vitro dissolution tests and are routinely applied for both product development and quality control. Drug dissolution testing is mostly conducted using recommended compendia methods and apparatus, such as the U.S. Pharmacopoeia and the European Pharmacopoeia e.g. USP 34 <711> and EP 7.2, 2.9.3. The FDA website provides extensive information on existing dissolution methods, and its contents are herein incorporated by reference in its entirety.

Dissolution media typically used in such tests are for example water and buffers such as phosphate buffers or citrate buffers. Different types of dissolution apparatus, based on different agitation methods are available commercially and are recognized by the compendia methods. These apparatus include: paddle, basket, flow-through, and reciprocating cylinder. While exact procedures (protocols) and apparatus vary, all drug dissolution test methods involve placing the pharmaceutical composition or dosage form into a dissolution medium and applying some agitation to the dissolution medium in order to promote disintegration and dissolution of the drug under test.

The dissolution medium and the detection method for determining the amount of the released drug in the dissolution medium depends upon (is chosen according) the chemical nature of the drug, and physical and stability considerations are also of great importance in making the appropriate choices.

Currently, there is no effective dissolution test for measuring the amount of API such as ivermectin with or without pyrantel in chewable, complex matrix, dosage forms. Moreover, the inventors are aware of no effective methods for measuring the amount of any hydrophobic API distributed in a similarly complex dosage form (e.g. medicated pet treats and the like). Finally, more and more API are being delivered to companion animals, including dogs and cats, in "treat form." Accordingly, there is a long-felt need to establish an effective dissolution method useful in dissolving complex matrix dosage forms for the subsequent quantification of APIs.

SUMMARY OF THE INVENTION

A dissolution method was developed to monitor the release profiles of hydrophobic active pharmaceutical ingredients such as ivermectin in combination with other API such as pyrantel pamoate (also hydrophobic) from a drug product made of complex matrix that includes but not limited to beef, tallow, corn cob and soy protein. Even though ivermectin (or related APIs individual or in combination with other actives) containing products have been on the market for many decades and there is no report on dissolution methods for such drug products.

The invention was unexpected and surprising, since typical USP/FDA in vitro dissolution medium compositions were not able to sufficiently disintegrate the complex chewable matrix dosage form containing ivermectin (with and without pyrantel). However, after extensive solvent property research and investigation, the most appropriate medium for complete chewable disintegration was selected and evaluated to wet and swell the chewable to facilitate dissolution.

Accordingly, in an embodiment, the disclosure describes the results of the studies conducted to develop a dissolution method to monitor release profiles of hydrophobic active pharmaceutical ingredients such as ivermectin and/or pyrantel pamoate from a drug product made of complex matrix that includes, but is not limited to beef, tallow, corn cob and soy protein.

In vitro dissolution testing of a solid dosage form such as a complex matrix solid dosage form, can be used for assessing batch-to-batch quality of a drug product, guide development of new formulations, ensure continuing product quality and performance after changes, such as changes in the formulation, the manufacturing process, the site of manufacture, and the scale-up of the manufacturing process, and testing of the shelf life of a product. In one aspect of the invention, the dissolution testing is used for assessing batch-to-batch quality of a solid dosage form. In another aspect of the invention, the dissolution testing is used for testing of the shelf life of a complicated matrix solid dosage form.

The solid dosage form is allowed to release the active ingredient in a period of time thereby forming at least a partial solution of the solid dosage form before withdrawing a sample.

Depending on the particular solid dosage form and e.g. the apparatus and the agitation chosen, the time before withdrawing the sample for determination of active ingredient will depend on the particular product to be tested and can be determined by a skilled person within the field. In one aspect of the invention, the solid dosage form is allowed to release the active ingredient for a period of time at least long enough for obtaining a homogenous solution making it possible to obtain reproducible results of tested samples.

After a certain time period at least some of the active ingredient has been released and the sample is can be filtered before determining the amount of active ingredient released at a given time period.

In one aspect of the invention, the sampling is performed within 24 hours of placing the solid dosage form in the dissolution apparatus. In a further aspect of the invention, the sampling is performed within 20 hours of placing the solid dosage form in the dissolution apparatus. In yet a further aspect of the invention, the sampling is performed within 16 hours of placing the solid dosage form in the dissolution apparatus. In yet a further aspect of the invention, the sampling is performed within 8 hours or within 2 hours of placing the solid dosage form in the dissolution apparatus.

Depending on the drug product to be tested, single point specifications, two point specifications or dissolution profiles can be used as described in e.g. U.S. Pharmacopeia (USP) 28 <711> and European Pharmacopoeia (EP) 5.0, 2.9.3. Typically single point specifications are used for routine quality testing for highly soluble and rapidly dissolving drug products. Two point specifications are typically used for characterizing the quality and as routine quality control testing of controlled release dosage forms.

Any apparatus suitable for dissolution of a drug product can be used. However, Applicants demonstrate herein that Apparatus 3 (reciprocating cylinder method) is particularly effective in carrying out the disclosed dissolution method.

In many cases it will be desirable to obtain a suitable in vivo correlation with in vitro release data and the final choice of any of these current methodologies or other alternatives/modifications will depend on the particular drug product to be tested. Above mentioned dissolution methodologies and apparatus can generally be used either with manual sampling or with automated procedures. In one aspect of the invention, the reciprocating cylinder method is used with either manual or automatic sampling.

After having immersed the drug product in a suitable dissolution vessel, in general mild agitation conditions should be maintained during dissolution testing in order to avoid or minimize foaming, and at the same time obtain a homogenously distribution in the vessel. Using the reciprocating cylinder method, the agitation (in dips per minute, DPM) is generally 5-60 dpm and with the paddle method, it is generally 50-150 rpm. In one aspect of the invention, the dissolution apparatus is a reciprocating cylinder apparatus. The volume of the dissolution medium is generally 500, 900, or 1000 mL. However, any appropriate volume may be chosen.

Any appropriate method for determining the amount of active ingredient may be used which is suitable in relation to the active ingredient to be measured and the dissolution medium. In a particular embodiment, HPLC is used to assay the amount of API.

BRIEF DESCRIPTION OF THE DRAWING

FIG. 1 is a graph depicting typical dissolution profiles for pyrantel pamoate and ivermectin chewables.

DETAILED DESCRIPTION OF THE INVENTION

In one aspect, the disclosure provides compositions for dissolving complicated matrices containing one or more hydrophobic active pharmaceutical ingredients (API).

In another aspect, the disclosure provides methods for dissolving complicated matrices containing one or more hydrophobic active pharmaceutical ingredients (API).

In an embodiment, the dissolution medium comprises from about 60% to about 99% NaOH aqueous solution, or a substantially equivalent amount of another similar base (e.g. KOH, LiOH, and $(NH_4)OH)$), and from about 5% to about 40% organic solvent.

In an embodiment, the organic solvent is selected from DMI, dioxane, THF, DMSO and any other similar organic solvent. In a preferred embodiment, the organic solvent is a cyclic ether. Now that Applicants have made the instant disclosure, it is

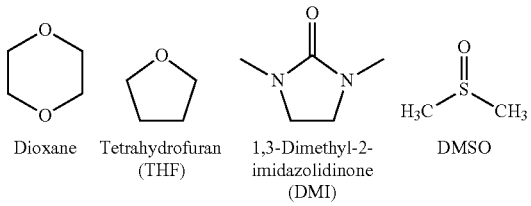

Dioxane    Tetrahydrofuran    1,3-Dimethyl-2-    DMSO
           (THF)              imidazolidinone
                              (DMI)

envisioned that any other suitable organic solvent may be routinely identified by those having ordinary skill in the art.

In yet another embodiment, the organic solvent is dioxane, DMI, THF, DMSO, or any combination thereof.

In a particular embodiment, the organic solvent is dioxane, DMI or a combination of both.

In a particular embodiment, the organic solvent is dioxane, THF or a combination of both.

In another particular embodiment, the organic solvent is DMI, THF or a combination of both. If DMI is used, it may be more effective when combined with THF, dioxane, or another cyclic ether.

In an embodiment, the dissolution medium comprises about 60% 1M NaOH in water and about 40% dioxane.

In another embodiment, the dissolution medium comprises about 70% 1M NaOH in water and about 30% dioxane.

In another embodiment, the dissolution medium comprises about 80% 1M NaOH in water and about 20% dioxane.

In another embodiment, the dissolution medium comprises about 85% 1M NaOH in water and about 15% dioxane.

In another embodiment, the dissolution medium comprises about 90% 1M NaOH in water and about 10% dioxane.

In another embodiment, the dissolution medium comprises about 95% 1M NaOH in water and about 5% dioxane.

In still another embodiment, the dissolution medium comprises or consists essentially of about 70% NaOH in water, about 15% dioxane and about 15% DMI.

Definitions

As used herein, "DMI" means 1,3-Dimethyl-2-imidazolidinone; "THF" means Tetrahydrofuran; "DMSO" means Dimethyl Sulfoxide; "IPA" means isopropyl alcohol; "PG" means propylene glycol; "DMF" means dimethylformamide; CTAB means Cetyltrimethylammonium Bromide; SDS means Sodium Dodecyl Sulfate; FaSSIF means Fasted State Simulated Intestinal Fluid; FeSSIF means Fed State Simulated Intestinal Fluid; NMP means N-Methyl-2-pyrrolidone; GF means Glycerol Formal; and GHP means Hydrophilic Polypropylene.

EXAMPLE 1

Experimental

In the early phase of method development and prior to performing dissolution analysis, soaking experiments were performed using prepared medium. The soaking experiments consisted of placing a chewable within each prepared medium and applying agitation. These experiments expedited the development medium selection process by using a smaller amount of medium (typically 50-100 mL whereas 1-2 L medium is needed for dissolution) while providing more vigorous conditions to yield faster disintegration observations for potential medium selection. Soaking experiments significantly reduced solvent consumption and expedited the medium identification process.

These experiments were conducted by preparing various medium compositions of surfactants (e.g. SDS, CTAB, and Tween 80) at various concentrations (e.g. ranging from 1% to 10%), and at various pH values within the physiological range (e.g. pH 1.2 to 7.4) as well as basic conditions (e.g. pH 10 and higher). Additionally, simulated gastric fluid, simulated intestinal fluids (i.e. FaSSIF and FeSSIF), organic solvents (e.g. dimethyl sulfoxide, dioxane and methanol), varying salt ionic strengths (e.g. acetate and phosphate), buffer concentrations (e.g. 0.01M to 10M), weak and strong acids, weak and strong bases, enzymes, and combinations thereof were evaluated as soaking media.

Results and Discussion

Table 1 summarizes the soaking experiments for all of the conditions evaluated. The soaking experiments were ranked into three Categories of 1) least promising medium [no significant (i.e., less than 10%) to ~50% disintegration within 24 hours], 2) somewhat promising medium (between ~50% to ~75% disintegration within 24 hours) and 3) most promising medium (greater than ~75% disintegration within 24 hours). From Table 1, the soaking experiments identified Conditions #1 to #46 as Category 1, Conditions #47 to #56 as Category 2 and Conditions #57 to #66 as Category 3.

TABLE 1

Summary of Soaking Experiments for Medium Selection

| # | Soaking Medium Description | Chewable Observations | General Comments |
|---|---|---|---|
| 1 | 40% Water/60% IPA | No significant disintegration (NSD); 24 hrs | Light, yellow solution; chew intact - "A" |
| 2 | 40% Water/60% Methanol | | |
| 3 | 40% Water/60% Acetone | | |
| 4 | 40% Water/60% PG | | |
| 5 | 40% Water/60% Ethanol | | |
| 6 | 40% Water/60% DMSO | | |
| 7 | 40% Water/60% DMF | | |
| 8 | 40% Water/60% THF | NSD; 24 hrs | Light, pink solution; chew intact |
| 9 | 100% Propylene Carbonate | NSD; 24 hrs | Light, yellow solution; floating chew intact |
| 10 | 100% Propylene Glycol | NSD; 24 hrs | "A" |
| 11 | 85% Phosphoric Acid in Water | | |
| 12 | 1M NaCl in Water | NSD; 48 hrs | Light, brown solution; chew intact |
| 13 | Concentrated Glacial Acetic Acid in Water | NSD; 24 hrs | "A" |
| 14 | 0.1N HCl in Water | NSD; 24 hrs | Light, brown solution; chew intact |
| 15 | 2M NaCl in Water | NSD; 48 hrs | Light, brown solution; chew intact |
| 16 | 80% 0.01M Mg(OH)$_2$ in Water/20% Dioxane | Not evaluated | Experiment canceled due to insolubility of Mg(OH)$_2$ in water |
| 17 | 10 mM Ammonium Formate in Water | ~10% D; 24 hrs | Light brown solution with some debris; ~90% chew intact |
| 18 | 10% SDS in Water | ~10% D; 48 hrs | Dark brown solution with some debris; ~90% chew intact |
| 19 | Brand Name Detergent | ~10% D; 48 hrs | Light brown solution with some debris; ~90% chew intact |
| 20 | 1% CTAB in Water | ~10% D; 48 hrs | Light, yellow solution; ~90% chew intact |
| 21 | 2% Tween 80 in Water | ~10% D; 48 hrs | Light brown solution with some debris; ~90% chew intact |
| 22 | FaSSIF | ~10% D; 48 hrs | Light yellow solution with some debris; ~90% chew intact |
| 23 | FeSSIF | ~10% D; 48 hrs | Light yellow solution with some debris; ~90% chew intact |
| 24 | 1N HCl in Water | ~10% D; 24 hrs | Brown solution with debris; ~90% chew intact |
| 25 | Concentrated Ammonium Hydroxide | ~10% D; 24 hrs | Light brown solution with debris; ~90% chew intact |
| 26 | 70% 1M NaOH in Water/ 30% NMP | ~10% D; 24 hrs | Dark brown solution with debris; ~90% chew intact |
| 27 | 70% 1M NaOH in Water/ 30% GF | ~10% D; 24 hrs | Dark brown solution with debris; ~90% chew intact |
| 28 | 70% Water in Water/ 30% Dioxane | ~10% D; 24 hrs | Light yellow solution with some debris; ~90% chew intact |
| 29 | 70% Water/30% GF | ~10% D; 24 hrs | |
| 30 | 5M NaCl in Water | ~10% D; 24 hrs | |

TABLE 1-continued

Summary of Soaking Experiments for Medium Selection

| # | Soaking Medium Description | Chewable Observations | General Comments |
|---|---|---|---|
| 31 | 80% 1M Tributylamine in Water/20% Dioxane | ~10% D; 48 hrs | Light yellow two-phase solution with some debris; ~90% chew intact |
| 32 | 1M TRIS in Water | ~20% D; 48 hrs | Brown solution with some debris; ~80% chew intact |
| 33 | 2.5M TRIS in Water/5% SDS in Water | ~20% D; 48 hrs | |
| 34 | 1M TRIS in Water/10% Brand Name Detergent | ~20% D; 48 hrs | |
| 35 | 2% SDS in 0.025M Sodium Phosphate Buffer pH 6.8 | ~25% D; 24 hrs | Dark brown solution with some debris; ~75% chew intact |
| 36 | 100% Water | ~25% D; 24 hrs | |
| 37 | 2% SDS in 0.025M Sodium Phosphate Buffer at pH 6.8/20% PC/10% IPA | ~25% D; 24 hrs | |
| 38 | 0.1M NaOH in Water | ~25% D; 24 hrs | Dark brown solution with debris; ~75% chew intact Complete disintegration at 26 hr time point |
| 39 | Concentrated Sulfuric Acid in Water | ~25% D; 24 hrs | Dark black solution with debris; ~75% floating chew intact |
| 40 | Simulated Intestinal Fluid | ~25% D; 24 hrs | Dark brown solution with white "tassels" clinging to chewable; ~75% chew intact |
| 41 | 70% 1M NaOH in Water/30% Propylene Glycol | ~25% D; 20 hrs | Dark brown solution with debris; ~75% chew intact |
| 42 | 70% 1M NaOH in Water/30% DMI | ~25% D occurred over 20 hrs. | |
| 43 | 80% 0.01M Ca(OH)₂ in Water/20% Dioxane | ~25% D; 48 hrs | |
| 44 | 50% 5M NaOH in Water/50% MeOH | ~30% D; 24 hrs | Dark brown solution with debris; ~70% chew intact |
| 45 | 70% 1M NaOH in Water/15% Dioxane/15% MeOH | ~30% D; 24 hrs | Light brown solution with some debris; ~70% chew intact |
| 46 | Simulated Gastric Fluid | ~50% D occurred over 92 hrs. | Dark brown solution with white "tassels" clinging to chewable; ~50% chew intact |
| 47 | 1M NaOH/5M NaCl in Water | ~50% D; 24 hrs | Light yellow solution with some debris; ~50% chew intact |
| 48 | 70% 5M NaOH in Water/30% DMSO | ~50% D; 24 hrs | Orange-brown solution with some debris; ~50% chew intact |
| 49 | 60% 1M NaOH in Water/20% Dioxane/20% Miglyol | ~50% D; 24 hrs | Two-phase system, orange-brown solution with some debris; ~50% chew intact |
| 50 | 70% 1M NaOH in Water/15% Dioxane/15% PG | ~50% D; 24 hrs | Light brown solution with some debris; ~50% chew intact |
| 51 | 70% 1M NaOH in Water/15% Dioxane/15% DMI | ~50% D; 24 hrs | Light brown solution with some debris; ~50% chew intact |
| 52 | 70% 1M NaOH in Water/15% MeOH/15% DMI | ~50% D; 24 hrs | Light brown solution with some debris; ~50% chew intact |
| 53 | 80% 1M Triethylamine in Water/20% Dioxane | ~50% D; 48 hrs | Light brown solution with some debris; ~50% chew intact |
| 54 | 70% 1M NaOH in Water/15% MeOH/15% PG | ~70% D; 24 hrs | Light yellow solution with some debris; ~50% chew intact |
| 55 | 70% 1M NaOH in Water/30% MeOH | ~75% D; 20 hrs | White foam on the surface of a dark brown solution with heavy debris; ~25% chew intact |
| 56 | 5M NaOH in Water | ~75% D; 24 hrs | Dark brown solution with heavy debris; ~25% chew intact |
| 57 | 1M NaOH in Water | ~80% D; 24 hrs | Dark brown solution with heavy debris; ~20% chew intact Complete disintegration at 26 hr time point |
| 58 | 70% 1M NaOH in Water/15% DMI/15% PG | ~80% D; 24 hrs. | Orange-brown solution with some debris; ~20% chew intact |
| 59 | 70% 1M NaOH in Water/30% Dioxane | ~100% D; 20 hrs. | Dark brown solution with heavy debris; chewable completely disintegrated |
| 60 | 70% 1M NaOH in Water/30% Miglyol | ~100% D; 20 hrs. | Two phase system, with white foam on top and dark brown solution on bottom with heavy debris; chewable completely disintegrated |
| 61 | 80% 1M NaOH in Water/20% MeOH | ~100% D; 24 hrs. | Dark brown solution with heavy debris, white surface foam present |
| 62 | 80% 5M NaOH in Water/20% MeOH | ~100% D; 24 hrs. | |
| 63 | 70% 1M NaOH in Water/30% MeOH | ~100% D; 24 hrs. | |
| 64 | 70% 5M NaOH in Water/30% MeOH | ~100% D; 24 hrs. | |

TABLE 1-continued

Summary of Soaking Experiments for Medium Selection

| # | Soaking Medium Description | Chewable Observations | General Comments |
|---|---|---|---|
| 65 | 80% 1M LiOH in Water/ 20% Dioxane | ~100% D; 48 hrs. | |
| 66 | 80% 1M KOH in Water/ 20% Dioxane | ~100% D; 44 hrs. | |

Once all of the soaking experiments were completed, the most favorable soaking media of Categories 2 and 3 were evaluated as dissolution media under typical dissolution operating conditions (e.g. ~500 mL, 37° C.) using USP Apparatus 2 (paddle apparatus) and USP Apparatus 3 (reciprocating cylinder). Table 2 summarizes the dissolution experiments using the chosen soaking media.

TABLE 2

Summary of Dissolution Experiments for Medium Selection (apparatus 3 was used for each of the following, except for condition 19, which used Apparatus 2)

| # | Dissolution Medium Description | Chewable Dissolution Visual Observations | General Comments |
|---|---|---|---|
| 1 | 95% 1N HCl in Water/5% Dioxane | ~10% D; 24 hrs | Light brown solution with some debris while ~90% chew intact |
| 2 | 85% 1N HCl in Water/15% Dioxane | ~10% D; 24 hrs | Light brown solution with some debris while ~90% chew intact |
| 3 | 95% 1N HCl in Water/5% THF | ~10% D; 24 hrs | Light brown solution with some debris while ~90% chew intact |
| 4 | 70% 1M NaOH in Water/15% MeOH/15% PG | ~30% D; 24 hrs | Orange-brown solution with some debris while ~80% chew intact Thick layer of white foam present on medium surface |
| 5 | 70% 1M NaOH in Water/15% Dioxane/15% MeOH | ~30% D; 24 hrs | Orange-brown solution with some debris while ~70% chew intact Thick layer of white foam present on medium surface |
| 6 | 70% 1M NaOH in Water/30% DMSO | ~50% D; 24 hrs | Orange-brown solution with some debris while ~50% chew intact |
| 7 | 1M NaOH/5M NaCl in Water | ~50% D; 24 hrs | Dark brown solution with heavy debris while ~50% chew intact |
| 9 | 70% 1M NaOH in Water/15% MeOH/15% DMI | ~50% D; 24 hrs | Orange-brown solution with some debris while ~50% chew intact Thick layer of white foam present on medium surface |
| 10 | 70% 1M NaOH in Water/15% DMI/15% PG | ~50% D; 24 hrs | Orange-brown solution with some debris while ~50% chew intact Thick layer of white foam present on medium surface |
| 11 | 70% 1M NaOH in Water/15% MeOH/15% DMI | ~60% D; 24 hrs | Orange-brown solution with some debris while ~40% chew intact Thick layer of white foam present on medium surface |
| 12 | 70% 1M NaOH in Water/30% MeOH | ~75% D; 24 hrs | Dark brown solution with heavy debris while ~25% chewable intact Thick layer of white foam present on medium surface |
| 13 | 95% 1M NaOH in Water/5% Dioxane | ~95% D; 20 hrs | Dark brown solution with heavy debris while ~5% chewable intact Thick layer of white foam present on medium surface |
| 14 | 1M NaOH in Water | ~100% D; 21 hrs | Dark brown solution with heavy debris, thick layer of white foam on medium surface using USP Apparatus 3 |
| 15 | 5M NaOH in Water | ~100% D; 20 hrs | Dark brown solution with heavy debris with complete disintegration No white foam on medium surface |
| 16 | 95% 1M NaOH in Water/5% THF | ~100% D; 20 hrs | Dark brown solution with heavy debris while chewable completely disintegrated Thick layer of white foam present on medium surface |
| 17 | 70% 1M NaOH in Water/30% Dioxane | ~100% D; 20 hrs | Dark brown solution with heavy debris while chewable completely disintegrated Thick layer of white foam present on medium surface |

TABLE 2-continued

Summary of Dissolution Experiments for Medium Selection (apparatus 3 was used for each of the following, except for condition 19, which used Apparatus 2)

| # | Dissolution Medium Description | Chewable Dissolution Visual Observations | General Comments |
|---|---|---|---|
| 18 | 70% 1M NaOH in Water/15% Dioxane/15% DMI | ~100% D; 24 hrs | Dark brown solution with heavy debris while chewable completely disintegrated Thick layer of white foam present on medium surface |
| 19 (A2) | 95% 1M NaOH in Water/5% Dioxane | ~100% D; 28 hrs | Dark brown solution with heavy debris No foam present on medium surface |
| 20 | 0.1N HCl in Water/1x Pepsin | ~25% D; 24 hrs | Orange-yellow solution with some debris while ~75% chew intact |
| 21 | 0.1N HCl in Water/5x Pepsin | ~75% D; 24 hrs | Orange-yellow solution with some debris while ~25% chew intact |
| 22 | 80% 1M NaOH in Water/20% Dioxane | ~100% D; 24 hrs | Dark brown solution with heavy debris while chewable completely disintegrated Thick layer of white foam present on medium surface |
| 23 | 60% 1M NaOH in Water/40% Dioxane | ~100% D; 24 hrs | Dark brown solution with heavy debris while chewable completely disintegrated Thin layer of white foam present on medium surface |

These visual disintegration and dissolution results confirm the complexity of the matrix, and demonstrate that the typical USP/FDA in vitro dissolution medium compositions are not appropriate for this type of drug product.

The soaking and dissolution experiments identified NaOH (or other substantially equivalent base) to be a key driver in the dissolution medium to disintegrate the chewables. Effectiveness of NaOH or another base in disintegrating the chewable is due to the ionization of the terminal amino acids of the beef protein and hence facilitating the rate of solvent sieving and or absorption by the matrix material of the chewable. NaOH is also reacting and neutralizing the beef tallow via classical saponification reaction which is also helping the chewables to absorb polar solvents and then disintegrate.

The majority of dissolution experiments were performed using USP Apparatus 3 as it provides strongest agitation (thus higher probability of disintegration at faster rate) for the products that are difficult to disintegrate. USP Apparatus 3 showed effective dissolution within 24 hours for several media. The heavy foam formation on the top of the dissolution vessels causes a challenge in sampling during dissolution. These challenges can be brought under control by using larger dissolution medium volume.

USP Apparatus 2 (paddle) also showed complete disintegration of chewables under same media conditions but the test duration was longer (excess of 24 hours).

TABLE 3

USP Apparatus 3 characteristics

| | USP Apparatus 3 |
|---|---|
| Stroke Length | 10 cm |
| Dip per Minute (DPM) | 5-60 dpm |
| Vessel Volumes | 100 mL, 300 mL, 1 L |
| Holders | Reciprocating Cylinders |
| Applications | Tablets, capsules, beads, chewables |

Based on extensive investigations, dissolution conditions stated in Table 4 were selected for the method. NaOH in combination with an organic solvent (e.g., Dioxane, THF, etc.) was surprisingly found to be suitable to monitor the release profiles of hydrophobic active pharmaceutical ingredients such as ivermectin along with API such as pyrantel pamoate from a drug product made of complex matrix. Cyclic ethers such as THF and dioxane have both a hydrophobic part and an oxygen with lone pairs of electrons (i.e. it is polar in nature). As such, these types of solvents effectively interact with a complex matrix composed of beef, tallow, corn cob and soy protein.

The inventors have surprisingly found that the ratio of NaOH (or a suitable equivalent thereof) with an organic solvent is critical to achieve product disintegrations, as well as to prevent the hydrophobic active pharmaceutical ingredients (such as ivermectin and pyrantel pamoate) from precipitating. Sample solutions at various time points were analyzed using HPLC methods to generate dissolution profiles as shown in FIG. 1.

TABLE 4

Dissolution Conditions

| USP Apparatus | USP Apparatus 3 (Reciprocating Cylinder) |
|---|---|
| Medium | 80% 1M NaOH in Water: 20% Dioxane |
| Medium Volume | 1-L for all chewable dosage sizes |
| Water Bath and Vessel Temperature | 37.0° C. ± 0.5° C. |
| Agitation Speed | 55 DPM |
| Sampling Times | 2, 4, 6, 8, 10, 12, 14 and 24 hours |
| Sample Volume | 5-mL at each sampling time |
| Medium Replacement | No replacement |
| Sample Filters | Cannula 1 micron poroplast, ⅛ pore size; Pall 25 mm syringe filter with 0.45 mm GHP membrane |

Conclusion. After extensive evaluation, a dissolution method was successfully developed to monitor the release profiles of hydrophobic active pharmaceutical ingredients such as ivermectin along with API such as pyrantel pamoate from a drug product made of complex matrix that includes but not limited to beef, tallow, corn cob and soy protein. The method developed is scientifically valid, and suitable for the purpose.

EXAMPLE 2

HPLC Measurement

Summary. This following method may be used for dissolution of API such as ivermectin (with or without pyrantel pamoate) in Chewables.

The dissolution of ivermectin and pyrantel pamoate from the chewable was achieved using the disclosed method: agitation with USP Apparatus 3 (reciprocating cylinder) at 55 DPM for 24 hours in 1-L of dissolution medium, comprised of 80% 1M sodium hydroxide in water and 20% dioxane. A specimen was withdrawn from each vessel at the designated sampling time points utilizing a stainless steel dissolution cannula. The specimen filtrate was collected using a 0.45 µm GHP syringe filter (particularly useful for adsorbing the proteins). The specimen filtrate is then analyzed by appropriate HPLC analyses to determine the dissolved amounts of ivermectin and pyrantel pamoate.

Equipment
- a. An HPLC system equipped with UV detection or a photodiode array detector, a column heater capable of maintaining a temperature, an injector, and a data system capable of performing data collection, integration and processing of chromatographic data.
- b. Analytical balance with the precision of at least 0.01 mg
- c. Graduated cylinders, class A or calibrated dispensers of equivalent or better accuracy
- d. Dissolution test system equipped with USP Apparatus 3 (reciprocating cylinder)
- e. Mechanical Stirrers/Stir Plates
- f. Stainless steel dissolution cannulas, equipped with Luer-Lock fittings
- g. Syringe filters, 25 mm, GHP, 0.45 µm
- h. Syringes, 5-mL, plastic and equipped with Luer-Lock
- i. Timer
- j. Thermometer
- k. Evaporation caps and covers
- l. Lower and upper reciprocating cylinder caps
- m. 10-mesh and 20-mesh stainless steel screens Materials

TABLE 5

List of materials used in the dissolution method

| Materials | Brand/Grade* |
|---|---|
| Water (H$_2$O) | MilliQ, USP or equivalent$^£$ |
| Dioxane | ACS Grade or equivalent |
| Sodium Hydroxide Pellets (NaOH) | ACS Grade or equivalent |
| Ivermectin | Reference Standard of known purity |
| Pyrantel Pamoate | Reference Standard of known purity |

*Equivalent or higher purity from different vendors can be used
$^£$Any pure quality water can be used provided there are no interfering or unexpected peaks in blank injection of the water Dissolution Conditions

TABLE 6

Dissolution Conditions

| Apparatus | USP Apparatus 3 (reciprocating cylinder) |
|---|---|
| Medium Volume | 1-L for all chewable dosage sizes |
| Water Bath & Vessel Temps | 37.0° C. ± 0.5° C. |
| Agitation Speed | 55 DPM |
| Sampling Times$^e$ | 2, 4, 6, 8, 10, 12, 14 and 24 hours |
| Sample Volume | 5-mL at each designated sampling time |
| Medium Replacement | No replacement |
| Sample Filter | 25 mm, GHP, 0.45 µm |

$^e$The sampling times represent a complete dissolution profile. A single sampling time (e.g. Q time point) can be used during routine analysis.

HPLC Conditions

Appropriate HPLC conditions were used to analyze ivermectin and pyrantel pamoate.

Solution Preparation

The dissolution medium was prepared according to the following, though the preparation may be scaled up or down proportionally, as long as the proportion of components remains substantially the same:

1. Dissolution Medium: (80% 1M Sodium Hydroxide in Water: 20% Dioxane) Example of Preparation: Dissolve 400 grams of sodium hydroxide pellets in 8 liters of water. Add 2 liters of dioxane and mix thoroughly.

2. Standard Preparation: Using dissolution medium prepare standard solutions of pyrantel pamoate and ivermectin at appropriate concentration that are suitable to analyze samples using HPLC.

3. Dissolution Sample Preparation:
- a. Visually inspect the dissolution test apparatus to ensure it is set up properly. Verify the water bath contains an appropriate volume to maintain the temperature of the vessel contents at 37.0° C.±0.5° C. throughout the entire test. Additionally, visually inspect and verify the apparatus and test materials for cracks, leaks and cleanliness;
- b. Dispense 1-L of dissolution medium into each of six vessels. Cover the vessels with the evaporation covers and ensure the water bath evaporation tarp (if installed) is in place;
- c. Equilibrate the water bath and dissolution medium in each vessel to 37.0° C.±0.5° C. Record the temperature of each vessel and the water bath;
- d. Equip each of the six syringes with stainless steel sampling cannulas;
- e. Randomly select six chewables and examine them to verify that each is intact, not chipped, cracked or split. Accurately weigh each chewable and record the weight;
- f. Equip each upper cap with 20-mesh stainless steel screens and each lower cap with 10-mesh stainless steel screens. Tightly secure the lower caps to their glass 100 mm reciprocating cylinders. Hold the reciprocating cylinder horizontally and slide the chewable into their respective reciprocating cylinders so the chewable rests atop the lower cap screen. Tightly secure the upper caps to the reciprocating cylinders;
- g. Move the BIO-DIS drive head into position over the designated row. Once the dissolution medium in each of the vessels have equilibrated to 37.0° C.±0.5° C., securely equip the reciprocating shafts with their evaporation caps, O-rings and the assembled reciprocating cylinders ensuring they are vertically centered;
- h. Begin the dip test and ensure the reciprocating cylinders are vertically centered upon immersion through the evaporation covers into the vessels. Also, ensure the evaporation caps fit securely against the evaporation covers to minimize evaporation throughout the test;
i. At the 2 hour designated time-point, pause the reciprocation by raising the reciprocating cylinders from the vessels. Allow a hold drip time of ~15 seconds. Lower the sampling cannulas into the dissolution medium and withdraw the specimen from a zone midway centered between the medium surface and bottom of vessel. Ensure the sampling cannulas are not immersed in the dissolution medium until after the drip time. All vessels should be sampled within 1 minute;
j. Resume the test once all of the 2 hour sampling time point samples are withdrawn. Ensure the reciprocating cylinders are vertically centered upon immersion through the evaporation covers into the vessels. Also, ensure the evaporation caps fit securely against the evaporation covers to minimize evaporation throughout the test;
k. Remove the syringe from the cannula and equip each syringe with a syringe filter. Collect approximately 1 mL of the specimen filtrate into a HPLC vial. Securely cap the HPLC vial for analysis;
l. Discard the remainder of the filtrate and re-equip the same syringe onto its respective sampling cannula. Note: The same cannula-filter assembly and syringe can be used for their respective vessels throughout the entire dissolution test;
m. Repeat steps i, j, k and l at each of the remaining time points of 4, 6, 8, 10, 12, 14 and 24 hours; and
n. Record the temperature of the water bath and dissolution medium in each of the six vessels at test completion to ensure each vessel was maintained at 37.0° C.±0.5° C.

Calculations
For Single Point Analyte Concentration:
The concentration of the analyte at the $n^{th}$ time point is calculated by:

$$C_n = \frac{A_n}{A_s} \times \frac{W_s}{D_s} \times P$$

The analyte percent (%) dissolved at the $n^{th}$ time point is calculated by:

$$\% \, Dissolved_n = \left\{ C_n \times [1000 - V_r(n-1)] + V_r \sum_{i=1}^{n-1} C_i \right\} \times 100 / LC$$

Where:
$C_n$=Concentration of analyte at the $n^{th}$ time point (mg)
$A_n$=Analyte peak area in the sample chromatogram (at the $n^{th}$ time point)
$A_S$=Average peak area of analyte in the bracketing standard solutions
$W_S$=Weight of the Reference Standard (mg)
$D_S$=Dilution factor for Working Standard Solution
P=Purity of Reference Standard, expressed in decimal form
1000=Initial Volume of dissolution medium (mL)
LC=Analyte Label Claim (mg)
$V_r$=Volume of vessel specimen removed at each sampling time point (5 mL)

The percent dissolved calculations were per dosage unit (1 chewable) from the analyte theoretical label claim for the respective chewable weight and not from the actual recorded individual chewable weight. The weight of each chewable was recorded for information purposes only.

Refer to Table 7 for the calculation of analyte percent dissolved at each of the designated sampling time points.

TABLE 7

Analyte Percent Dissolved at Each Sampling Time Point

| Sampling Time | Percent (%) Dissolved Calculations |
| --- | --- |
| 2 hrs | % Dissolved$_2$ = C$_2$(1000) × 100/LC |
| 4 hrs | % Dissolved$_4$ = [C$_4$(995) + 5 × C$_2$] × 100/LC |
| 6 hrs | % Dissolved$_6$ = [C$_6$(990) + 5 × (C$_2$ + C$_4$)] × 100/LC |
| 8 hrs | % Dissolved$_8$ = [C$_8$(885) + 5 × (C$_2$ + C$_4$ + C$_6$)] × 100/LC |
| 10 hrs | % Dissolved$_{10}$ = [C$_{10}$(880) + 5 × (C$_2$ + C$_4$ +C$_6$ + C$_8$)] × 100/LC |
| 12 hrs | % Dissolved$_{12}$ = [C$_{12}$(875) + 5 × (C$_2$ + C$_4$ + C$_6$ + C$_8$ + C$_{10}$)] × 100/LC |
| 14 hrs | % Dissolved$_{14}$ = [C$_{14}$(870) + 5 × (C$_2$ + C$_4$ + C$_6$ + C$_8$ + C$_{10}$ + C$_{12}$)] × 100/LC |
| 24 hrs | % Dissolved$_{24}$ = [C2$_4$(865) + 5 × (C$_2$ + C$_4$ + C$_6$ + C$_8$ + C$_{10}$ + C$_{12}$ + C$_{14}$)] × 100/LC |

Use theoretical label claim as per Table 8 for calculations:

TABLE 8

Chewable Label Claim

| Theoretical Ivermectin μg/chewable | Theoretical Pyrantel Pamoate mg/chewable |
| --- | --- |
| 34.0 | 81.0 |
| 68.0 | 163.0 |
| 136.0 | 326.0 |
| 272.0 | 652.0 |

What is claimed:
1. A method for determining the amount of at least one hydrophobic active pharmaceutical ingredient (API) released from a pharmaceutical solid dosage form, said method comprising the steps of:
   a. allowing said solid dosage form to release the active ingredient in a dissolution medium comprising:
      i. from about 60% to about 90% 1M NaOH, 1M LiOH or 1M KOH in water; and
      ii. from about 10% to about 40% of an organic solvent; and
   b. determining the amount of active ingredient in the dissolution medium.
2. The method of claim 1, wherein the dissolution medium comprises greater than about 10% of the organic solvent.

3. The method of claim 2, wherein the dissolution medium comprises greater than about 15% of the organic solvent.

4. The method of claim 3, wherein the dissolution medium comprises greater than about 20% of the organic solvent.

5. The method of claim 4, wherein the dissolution medium comprises greater than about 25% of the organic solvent.

6. The method of claim 1, wherein the organic solvent is selected from dioxane, DMI, DMSO, THF, and combinations thereof.

7. The method of claim 6, wherein the 1M NaOH in water is present in an amount of about 80% and the organic solvent is present in an amount of about 20%.

8. The method of claim 7, wherein the organic solvent is dioxane.

9. The method of claim 1, wherein the release of active ingredient is carried out in a dissolution apparatus selected from a reciprocating cylinder and a paddle apparatus.

10. The method of claim 9, wherein the dissolution apparatus is a reciprocating cylinder, which is set to agitate at between about 50 and 60 dips per minute (dpm).

11. The method of claim 1, wherein the solid dosage form comprises one or more of beef, tallow, corn cob or soy protein.

12. The method of claim 11, wherein the solid dosage form comprises beef, tallow, corn cob and soy protein.

13. The method of claim 11, wherein the method comprises sampling the dissolution medium within 24 hours of placing the solid dosage form in the dissolution medium.

14. A method for dissolution testing of a solid dosage form containing one or more active pharmaceutical ingredient(s) comprising:
   a. filling a vessel with between about 300 ml and about 1000 ml of dissolution medium comprising from about 60% to about 90% 1M NaOH, 1M LiOH or 1M KOH in water and from about 10% to about 40% of an organic solvent;
   b. raising the temperature of the dissolution medium;
   c. depositing the dosage form within the vessel;
   d. engaging a reciprocating cylinder at an agitation speed between about 50 dpm and 60 dpm;
   e. allowing the dosage form to completely dissolve over about 24 hours; and
   f. measuring the concentration of the active pharmaceutical ingredient(s) using HPLC.

* * * * *